United States Patent [19]

Yamamoto et al.

[11] 4,273,535

[45] Jun. 16, 1981

[54] DEVICE FOR PREVENTING TOOTH DECAY BY LASER BEAM IRRADIATION AND METHOD OF PREVENTING TOOTH DECAY BY USE OF THE SAME

[75] Inventors: Hajime Yamamoto, Izumi; Shogo Yoshikawa, Kawasaki, both of Japan

[73] Assignee: Kabushiki Kaisha Morita Seisakusho, Kyoto, Japan

[21] Appl. No.: 75,645

[22] Filed: Sep. 14, 1979

[30] Foreign Application Priority Data

Dec. 4, 1978 [JP] Japan ............................. 53/150402

[51] Int. Cl.³ .......................... A61C 3/00; A61C 19/06
[52] U.S. Cl. ................................... 433/216; 433/215; 433/25; 433/141; 128/303.1
[58] Field of Search ................. 433/216, 215, 25, 141; 128/303.1

[56] References Cited

U.S. PATENT DOCUMENTS

| 4,141,362 | 2/1979 | Wurster ............................. 128/303.1 |
| 4,185,633 | 1/1980 | Prozorov et al. ................. 128/303.1 |

OTHER PUBLICATIONS

"Dentistry and the Laser", by Ralph H. Stern, in *Laser Applications in Medicine and Biology*, vol. 2, ed. M. L. Wolbausht (1974).

*Primary Examiner*—Gene Mancene
*Assistant Examiner*—Michael J. Foycik
*Attorney, Agent, or Firm*—Koda and Androlia

[57] ABSTRACT

The disclosure relates to a device for preventing tooth decay by use of laser beams and to a method of preventing tooth decay by use of such a device. According to the invention, high-speed repetition pulses projected from Q-switched continuous excitation Nd:YAG laser is irradiated upon teeth through a glass beam guide, whereby treatment of the teeth is reduced in time, is safe, effective and is readily useable for use by general practice.

4 Claims, 1 Drawing Figure

DEVICE FOR PREVENTING TOOTH DECAY BY LASER BEAM IRRADIATION AND METHOD OF PREVENTING TOOTH DECAY BY USE OF THE SAME

BACKGROUND OF THE INVENTION

1. Field of the Invention

This invention relates to a device for the prevention of tooth decay and to a method of preventing tooth decay by use of such a device.

2. Prior Art

Prevention of tooth decay is important for good health and a variety of preventive methods have heretofore been used. But nevertheless, the rate of tooth decay is exceedingly high and, in particular, in the case of children the rate is as high as 90%. This fact indicates that it is difficult to impart perfect decay resistance to teeth by the conventional tooth decay prevention methods.

For clarity of description, the mechanical order of the development of a decayed tooth will now be described as follows: Generally, a region exposed above the tooth gum is called enamel, which consists chiefly of crystals of hydroxy apatite. The crystals abound in lattice defect and distortion. Also, the surface of the enamel appears very smooth to the naked eye, but it has been found through examination under an electronic scanning microscope, that the surface has tiny holes and side edges of deep-cut wavy stripes.

On the other hand, the inside of the mouth is a living place for various types of bacteria some of which function to dissolve sugar and produce lactic acid on the tooth surface. The lactic acid initially attacks the above-mentioned tiny holes and deep-cut peripheral side edges that exist inherently in the enamel and act on the hydroxy apatite, which is instable due to the lattice defect and distortion, and dissolves and decalcifies the hydroxy apatite and thereby destroys the enamel. This is the mechanical order in which teeth start to decay.

A description will now be given of the mechanical order of methods to prevent tooth decay heretofore in use. As is well known, the conventional methods are those in which fluorine was used. In these methods, a fluorine compound was brought into contact with the enamel of the teeth by the application of the fluorine compound to the teeth, whereby the fluorine ion (F—) is caused to act on the hydroxy apatite, which in turn, is changed into fluorapatite, which is resistant to acids and thereby prevents the decaying of the tooth enamel.

The conventional methods for preventing tooth decay described above is not free from disadvantages, which will now be discussed as follows: One of the disadvantages is that the above-mentioned methods are not always completely effective. As described above, in order to change hydroxy apatite into fluorapatite which is resistant to acids, a perfect reaction must be effected by bringing the fluorine ion (F—) sufficiently into contact with the crystal structures. But mere application of the fluorine compound to the enamel results in only a slight degree of formation of fluorapatite on the surface layer of the enamel with a strong possibility that the hydroxy apatite will not be fully fortified with a decay resistant property. Particularly, little or no fluorine ion (F—) goes into the enamel and no fluorapatite is produced at all. Accordingly, the remaining texture on the tooth surface is corroded by acids, melts and falls off to thereby bring a new hydroxy apatite texture into direct contact with acids, thus furthering the state of tooth decay, contrary to the original intention. It has been found in the present invention that the afore-mentioned tiny holes and peripheral side edges existing in the tooth enamel are a target area of tooth decay and that accordingly, as long as the tiny holes and side edges exist, no perfect result can be expected from the conventional tooth decay prevention methods in which fluorine is used. Another disadvantage inherent in the conventional methods is that these methods lack continuity in their effectiveness so that they need to have repeated applications of fluorine. This disadvantage, as previously pointed out, is due to the fact that it is difficult to create a sufficient chemical reaction from a single application of fluorine and that accordingly, a texture sufficient for effective prevention of tooth decay is apt to be lacking.

On the other hand, a method of irradiating giant pulses produced from Q-switched flash lamp excitation Nd:YAG laser upon the teeth is published by the present inventors and is widely known as a method which can eradicate the preceding drawbacks of conventional tooth decay prevention methods and impart effective decay-resistant properties to the tooth enamel by a single operation. The new method reveals that irradiation of giant pulses of energy density less than the order of 40 J/cm$^2$ upon the teeth melts only a thin surface layer portion of the tooth enamel and thereby fills up the holes and peripheral wavy striped side edges existing on the tooth surface, thus eliminating the region subject to the initial attack of decay and increasing the decay-resistant properties of the teeth. The reason for the use of Nd:YAG laser as a laser oscillator is that the oscillation wavelength of this laser is 1.06 $\mu$m and this wavelength acts selectively on the tooth enamel and does the least harm to the other regions. But the use of the Q-switched flash lamp excitation Nd:YAG laser in the context of the present invention provides serious disadvantages that will hereinafter be discussed. Namely, the flash lamp excitation laser is as low as several to a hundred pulses per second and because the average output of the laser is small notwithstanding the fact the the energy per giant pulse is great. Therefore, the effect of radiation per unit time becomes small and consequently, operation time per tooth becomes long. Also, because the giant pulses of the flash lamp excitation laser are exceedingly high in pulse peak output, normally several to some ten MW, there is a danger that the irradiation of the laser beams upon the teeth causes damage to the tooth surface. Furthermore, when flexible glass fibers are used in the guide for leading the laser beams from the oscillator to the region to be operated on luminous damage occurs and the fibers cannot be used but recourse must be made to the multi-joint manipulator or the like, with the result that adjustments and the operation become complicated.

SUMMARY OF THE INVENTION

Accordingly, an object of this invention is to provide a device to prevent tooth decay which is short in treatment time, safe and positive in effect, can be readily used in general dental practice and which is characterized by the use of Q-switched continuous excitation Nd:YAG laser oscillator and by the use of flexible glass fibers as a means of guiding Q-switch pulses relatively small (several to some hundred KW) in projected pulse peak output and quick of repetition to the region to be treated and a method of preventing tooth decay by use of such a device.

Since the invention uses the continuous excitation Nd:YAG laser as an oscillator, the peak output of Q-switch pulses projected is smaller, more than one figure than the giant pulses from the flash lamp excitation laser, there is less danger of the radiation of the Nd:YAG laser beam upon the teeth causing damage to the tooth surface, and since the invention makes it possible to use flexible glass fibers as a laser beam guide, operational efficiency of the present invention is increased in clinical application. Also, since the repetition of Q-switch of continuous excitation Nd:YAG laser is possible, even to a degree of several ten kHz and its mean output amounts to the same degree (several ten to hundred W) as continuous oscillation output, the period of time for irradiation of the laser beams upon the teeth is reduced to a substantial degree.

A description will now be given of a preferred embodiment of the invention with reference to the drawing.

DETAILED DESCRIPTION OF THE INVENTION

Figure 1:
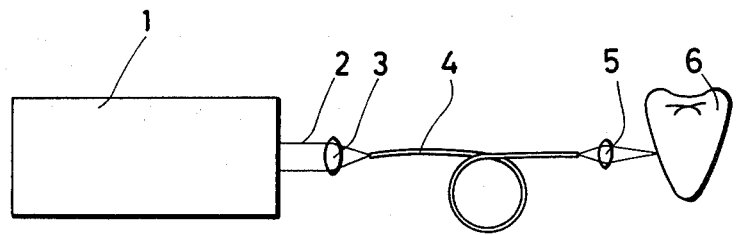
FIG. 1 is a diagram illustrating an embodiment of the invention wherein the Q-switched continuous excitation Nd:YAG laser and flexible glass fibers are used.

In FIG. 1 the laser beams 2 projected from a Q-switched continuous excitation Nd:YAG laser oscillator are caused by a condensing lens 3 to fall upon quartz glass fibers 4 having a core diameter of 300 μm and an outer diameter of 350 μm and capable of transmitting high output laser beams at a low rate of loss. Various methods and means have been developed of Q-switching continuous excitation Nd:YAG laser, and a method of using an ultrasonic modulator is particularly superior in that the loss of laser beams in inserting the modulator into the oscillator is small and in that the repetition frequency of the Q-switch can be optionally changed, and therefore, the ultrasonic Q-switch is used in the embodiment of the present invention. The high-speed repeated Q-switched photo-pulses transmitted by glass fibers 4 are again condensed by a condensing lens 5 and irradiated upon the teeth 6. Consequently, the surface layer the portion subject to the initial by high output and high density laser beam energy to eliminate the tiny holes and peripheral wavy striped side edges inherently existing on the surface of the tooth enamel and to remove the portion subject to the initial attack of decay, thus improving the decay-resistant properties of teeth.

The capacity of continuous excitation Nd:YAG laser used in the prefered embodiment is 100 W in continuous oscillation output, 100 KW in pulse peak output of Q-switch repetition frequency of 1 kHz in Q-switch operation by the ultrasonic modulator, 100 ns in pulse width, 10 mj in pulse energy, and 10 W in mean output. The experiments with this laser indicated that irradiation of laser beams upon the teeth for a period of less than several seconds in Q-switch repetition frequency of one to several kHz produced a marked effect on the decay-resistant properties teeth.

The present invention has confirmed that irradiation of these laser beams specified by the above conditions not only makes it possible to easily penetrate fluorine ion (F—) through the enamel surface layer and through the enamel interior by application of a fluorine compound in addition to the irradiation of the beams, but also enables instant production of fluorapatite inside the tooth enamel by laser energy. This finding has made it apparent that positive decay prevention can be obtained by the present invention. Also, since the present invention uses flexible glass fibers as a laser beam guide, it is superior in operational efficiency as to alignment of photoaxis, photo induction and the like. Clinical advantages acquired from the use of the present invention are far greater than the advantages of using a manipulator. Particularly, the use of a condensing type light path, so-called SELFOC would simplify the input and output optical system with respect to the fibers and would clinically be advantageous by reducing the device in size and weight.

It is further understood by those skilled in the art that the foregoing description is a preferred embodiment of the disclosed device and various changes and modifications may be made in the invention without departing from the spirit and scope thereof.

I claim:

1. A device for preventing tooth decay by irradiation of laser beams, said device comprising:
   a continuous excitation Nd:YAG laser oscillator having a mean output capacity of at least 10 watts and a peak output limited to less than 100 KW;
   an ultrasonic Q-switch for Q-switching said continuous excitation Nd:YAG laser at a rate from 1 to several kHz;
   a condensing lens means for transmitting Q-switch pulses projected from said oscillator;
   a transmitting means consisting of glass fibers for transmitting the thus condensed laser beams; and
   a condensing lens means for convergently irradiating the thus transmitted laser beams upon the tooth surface to be treated.

2. A device according to claim 1, wherein said glass fibers are quartz and are each 300 μm in core diameter and 350 μm in outer diameter.

3. A method of preventing decay in a human tooth by irradiation of laser beams, said method comprising:
   coating the surface of said tooth beforehand with a fluorine compound;
   generating Q-switch pulses by use of a continuous excitation Q-switched Nd:YAG laser oscillator having a peak output of less than 100 KW and a switching frequency of at least 100 kHz, condensing the thus generated Q-switched pulses and transmitting the same from said laser oscillator to said tooth by a transmitting means employing glass fibers and condensing the transmitted laser beam; and
   convergently irradiating the beams for up to several seconds upon said tooth surface.

4. A method according to claim 3, wherein said continuous excitation Nd:YAG laser is about 100 KW in its continuous oscillation output, about 100 KW in pulse peak output, 100 ns in pulse in pulse width, and about 10 mj in pulse energy.

* * * * *

UNITED STATES PATENT AND TRADEMARK OFFICE
Certificate

Patent No. 4,273,535            Patented June 16, 1981

Hajime Yamamoto and Shogo Yoshikawa

Application having been made by Hajime Yamamoto and Shogo Yoshikawa, the inventors named in the patent above identified, and Kabushiki Kaisha Morita Seisakusho, Kyoto-shi, Japan, the assignee, for the issuance of a certificate under the provisions of Title 35, Section 256, of the United States Code, adding the name of Sadayasu Ota as a joint inventor, and a showing and proof of facts satisfying the requirements of the said section having been submitted, it is this 18th day of May 1982, certified that the name of the said Sadayasu Ota is hereby added to the said patent as a joint inventor with the said Hajime Yamamoto and Shogo Yoshikawa.

Fred W. Sherling
*Associate Solicitor.*